(12) United States Patent
Bertram et al.

(10) Patent No.: US 7,377,960 B2
(45) Date of Patent: May 27, 2008

(54) CYCLONIC SEPARATOR WITH SECONDARY VORTEX BREAK

(75) Inventors: Jeff Bertram, St. Louis, MO (US); William J. Nelgner, St. Charles, MO (US)

(73) Assignee: Engineered Support Systems, Inc., St. Louis, MO (US)

( * ) Notice: Subject to any disclaimer, the term of this patent is extended or adjusted under 35 U.S.C. 154(b) by 456 days.

(21) Appl. No.: 11/058,666

(22) Filed: Feb. 15, 2005

(65) Prior Publication Data

US 2005/0223685 A1    Oct. 13, 2005

Related U.S. Application Data

(60) Provisional application No. 60/560,122, filed on Apr. 7, 2004.

(51) Int. Cl.
*B01D 45/12*    (2006.01)

(52) U.S. Cl. ............... 95/271; 55/424; 55/435; 55/439; 55/459.1; 55/466; 96/413

(58) Field of Classification Search ............ 55/345, 55/424, 428, 432, 435, 439, 459.1, 466; 95/271; 96/413
See application file for complete search history.

(56) References Cited

U.S. PATENT DOCUMENTS

| | | | |
|---|---|---|---|
| 5,453,196 A * | 9/1995 | Tuszko et al. ........... 210/512.1 |
| 6,425,931 B1 | 7/2002 | Croggon | |
| 6,482,246 B1 | 11/2002 | Dyson et al. | |
| 6,485,536 B1 | 11/2002 | Masters | |
| 6,506,311 B2 | 1/2003 | DeGarmo et al. | |
| 6,582,489 B2 | 6/2003 | Conrad et al. | |
| 6,596,046 B2 | 7/2003 | Conrad et al. | |
| 6,739,456 B2 | 5/2004 | Svoronos et al. | |
| 6,997,973 B2 | 2/2006 | Kilgore | |
| 7,125,437 B2 * | 10/2006 | Bryden et al. ............. 95/29 |

FOREIGN PATENT DOCUMENTS

DE    10023009 A1 *    12/2000

* cited by examiner

*Primary Examiner*—Robert A Hopkins
(74) *Attorney, Agent, or Firm*—Sonnenschein Nath & Rosenthal LLP

(57) ABSTRACT

A cyclonic separator and methods of cyclonic separation which provide for a band pass separation of particles. That is, a cyclonic separator able to remove particles from an air stream that are greater than a predetermined minimum (which is greater than zero) while being smaller than a particular maximum. This band pass separation may be performed with the inclusion of a secondary vortex break on a cyclonic separator. Also discussed are cyclonic flow systems which provide for less deposition of aerosolized particles onto the cyclonic flow generator and related structures to improve likelihood of particles of interest being provided to an attached detector.

19 Claims, 3 Drawing Sheets

CYCLONIC SEPARATOR WITH SECONDARY VORTEX BREAK

CROSS REFERENCE TO RELATED APPLICATION(S)

This Application claims the benefit of U.S. Provisional Patent Application Ser. No. 60/560,122, filed Apr. 7, 2004, the entire disclosure of which is herein incorporated by reference.

BACKGROUND

1. Field of the Invention

This disclosure relates to the field of cyclonic separators and the use of cyclonic flows to separate and isolate particles. In particular, this disclosure relates to the designs of cyclonic separator systems that allow particles in a particular size band to be collected and transferred to a separate flow as well as designs that lead to the reduction of particle buildup in the cyclonic flow generator and related components.

2. Background of the Invention

The cyclonic separator is a well known general technology having applications from scientific research to today's bagless vacuum cleaners. The principle of operation is theoretically quite simple; the cyclonic separator uses rotational motion, and changes in rotational motion velocity to precipitate particles out of an air flow. In the case of a vacuum cleaner, the cyclonic motion deposits particles of a particular size or larger into a collection bin, then returns the air flow to the outside. In this way the dust and particles captured by the vacuum cleaner can be collected and disposed of.

Since the use of anthrax in the United States mail in October 2001, government organizations have become increasingly interested in detecting dangerous substances such as microorganisms, chemicals, or biological warfare agents which could be unleashed on the United States to promote the agenda of a terrorist organization.

The transmission of agents is particularly of concern when used in aerosolized form where early detection may be difficult. Because large buildings, subway systems, and the like utilize air circulation systems in relatively self contained environments there is increasing concern that the ventilation systems of these environments could be used in an attack to spread a dangerous warfare agent quickly and in a manner that is difficult to detect. This scenario raises the level of interest in aerosolized contaminant detection.

The detection of aerosolized contaminants also commands great interest because it provides for a relatively easy and unobtrusive way to monitor objects which might contain a warfare agent. No matter how careful a person is, generally some particles of an agent are released into the atmosphere when that agent is being packed, transported, or loaded in preparation of its being unleashed. The inability to completely contain the agent has led to a plethora of searching devices to detect warfare agents as well as other potentially aerosolized substances released from the surface of an item. Bomb- or illegal drug-sniffing dogs searching for such residue on luggage or packages are one such technology of this type where the dog's nose can detect a minute amount of particles aerosolized by the object's passing.

Another way to obtain samples of particulates that may be present in or on an object, is to use air to directly aerosolize the residue and carry it to a detector. Air may be purposefully flowed over objects of interest to dislodge and collect the minute particles without risk of damage or loss of privacy. U.S. patent application Ser. No. 10/449,612, the entire disclosure of which is herein incorporated by reference, describes embodiments of a system for obtaining aerosolized samples of materials on or potentially included in mail.

One of the leading problems with aerosolized samples produced by these methods and even those produced through other actions, however, is that there is a large amount of air involved, even in a small application, and that air naturally includes a huge number of particles which are not of interest. Pollens, dust, pollutants, atmospheric microorganisms and other materials are always in the air to be sampled, thus making detection of the particles of interest more challenging.

Further, detectors sensitive to particular biological or chemical items of interest, generally have to process every particle they are provided with. As the air will naturally include many particles which are not of interest, it is desirable to separate out as many of those particles as possible before providing the air to the detector while still allowing particles potentially of interest to be provided to the detector. Uninteresting particles can clog the detector over time, increasing the amount of maintenance required or decreasing the detector's life. It is therefore desirable to remove them from the air stream provided to the detector.

Still further, to detect a multitude of chemical or biological materials, it may be necessary to have multiple different types of detectors. Each detector must process every particle in the air stream provided to it to determine its relevance. Where each detector is provided the air flow sequentially, detection may be too slow and cumbersome, especially where large air flow volumes need to be monitored. Further, depending on the type of detector, if too many uninteresting particles are present, detection of particles of interest could become too attenuated.

Because of problems such as the above, most chemical and biological systems utilize some form of particle separator to eliminate particles which are known to not be particles of interest. For example, if a particular microorganism is being sought to be detected, particles which are dramatically smaller or dramatically bigger than the microorganism do not need to be tested. Traditionally, the particles have been separated using filters or cyclonic separators. Both these systems have a very noticeable problem, however, in that they cannot provide particles in a size range that does not include one of the small or large size extremes. A cyclonic separator will trap all particles of the desired size and larger, whereas a filter can only allow passage of particles of the desired size and smaller, trapping those particles of a larger size. These methods also have the problem that they require regular checking to prevent clogging. In sum, this generally means that particles either above or below a particular size may be analyzed, but there is no reasonable way to get particles in a particular range or band.

These methods also have trouble in applications where there are a substantial number of particles present which are either larger or smaller than the particles of interest and which cannot be well separated by the chosen methodology. In particular, if the desired particle is quite small and the system is operating in a dusty environment where there are a large number of uninteresting particles of relatively large size, a cyclonic separator will generally provide too many particles to a detector, while a filter will rapidly become clogged and fail.

Beyond the problems of inefficient separation, there is also the problem that filter media and cyclonic separators will often stop particles of interest through deposition, either on the filter media (particularly if it is getting clogged) or on the surface of the cyclonic separator or related structures during the cyclonic separation. Such trapping of particles of interest means that trace amounts which may need to be detected, are instead confined to the separator and its related structures.

SUMMARY

Because of these and other problems in the art, described herein is a cyclonic separator which provides for a band pass separation of particles. That is, a cyclonic separator able to remove particles from an air stream that are greater than a predetermined minimum (which is greater than zero) while being smaller than a particular maximum. In an embodiment, this band pass separation is performed with the inclusion of a secondary vortex break on a cyclonic separator. Also disclosed herein are cyclonic flow systems which provide for less deposition of aerosolized particles onto the cyclonic flow generator and related structures to improve likelihood of particles of interest being provided to an attached detector.

In an embodiment, the cyclonic separator comprises a primary separator having an at-least-partially conical shape; a primary vortex break having a generally conical shape, and a secondary vortex break, wherein said secondary vortex break is generally not conical but may be cylindrical or of other volume in shape and has an output tube located on a side thereof. In an embodiment, the primary separator will be attached to the primary vortex break which is in turn attached to the secondary vortex break.

In an embodiment there is described herein, a cyclonic separator comprising: a primary separator; a primary vortex break attached to said cyclone; and a secondary vortex break, said secondary vortex break attached to said primary vortex break and having an output tube attached to a side thereof; wherein said cyclonic separator separates particles in a particular band from other particles, said band having a minimum size greater than zero and a maximum size; and wherein an air flow including a concentration of said particles in said band flows into said output tube.

In an embodiment of the cyclonic separator, the separator further comprises a fan for pulling air and suspending particles into said output tube.

In an embodiment of the cyclonic separator, the secondary vortex break is not in the shape of an inverted cone, while the primary vortex break or primary separator may be generally in the shape of an inverted cone.

In an embodiment of the cyclonic separator, the internal surface of at least one of said cyclone and said primary vortex break is rough and may have surface roughness between about 16 and about 500 micro inches.

In an embodiment of the cyclonic separator, the minimum size of the band is 0.85 micron while the maximum size is 12 microns. The concentration of said particles may include a chemical or biological warfare agent.

In an embodiment of the cyclonic separator, the separator is arranged vertically with said primary separator above said primary vortex break which is in turn above said secondary vortex break so that separation is partially accomplished by the force of gravity.

In an embodiment of the cyclonic separator, the secondary vortex break is in the shape of a cylinder and output tube is arranged either radially or tangentially to said cylinder and may lead to a detector.

In another embodiment, there is described, a method for cyclonic separation comprising: forming a first air flow, said first air flow being cyclonic; passing said air flow through a first choke point, said first air flow splitting into a second air flow which flows internal to said first air flow and a third air flow which interacts with slower moving air below said first choke point; having said third air flow and slower moving air pass through a second choke point and into a secondary vortex break; drawing said air in said secondary vortex break outward; and collecting at least a portion of said air which is drawn outward.

In another embodiment of the method, the air which is drawn outward includes suspended particles which may include chemical or biological warfare agents.

DESCRIPTION OF PREFERRED EMBODIMENT(S)

Figure 1:
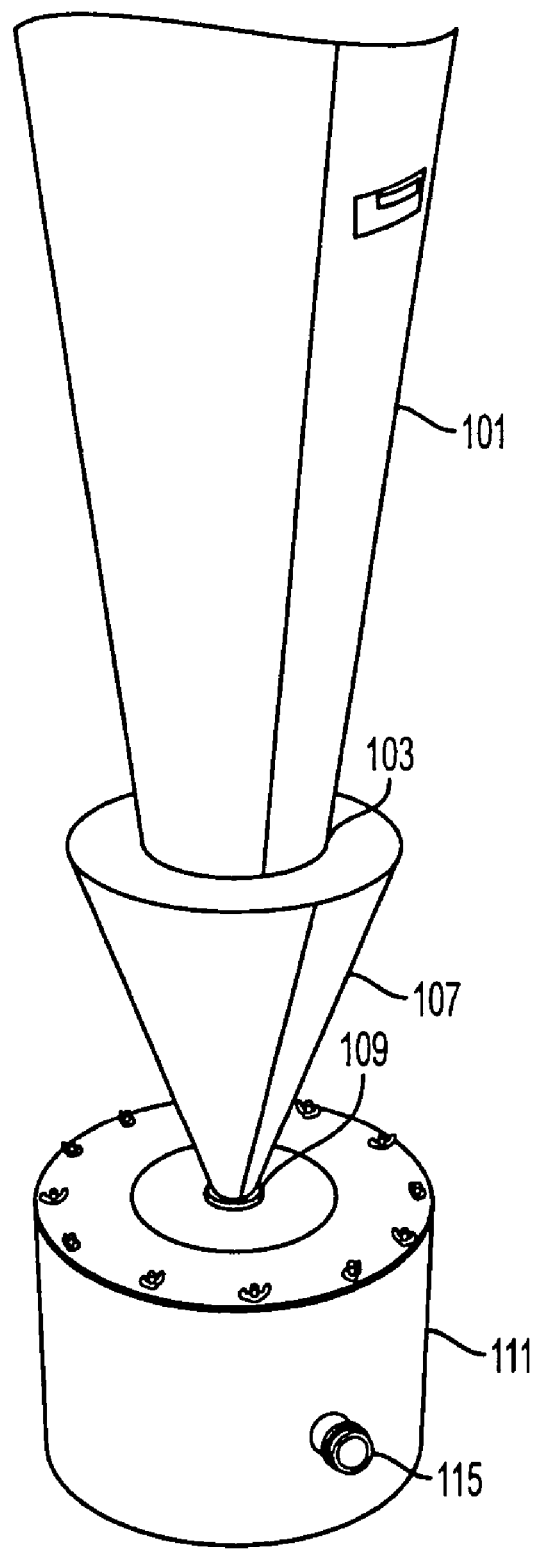
FIG. 1 provides a perspective view of an embodiment of a cyclonic flow separator system including a secondary vortex break.
Figure 2:
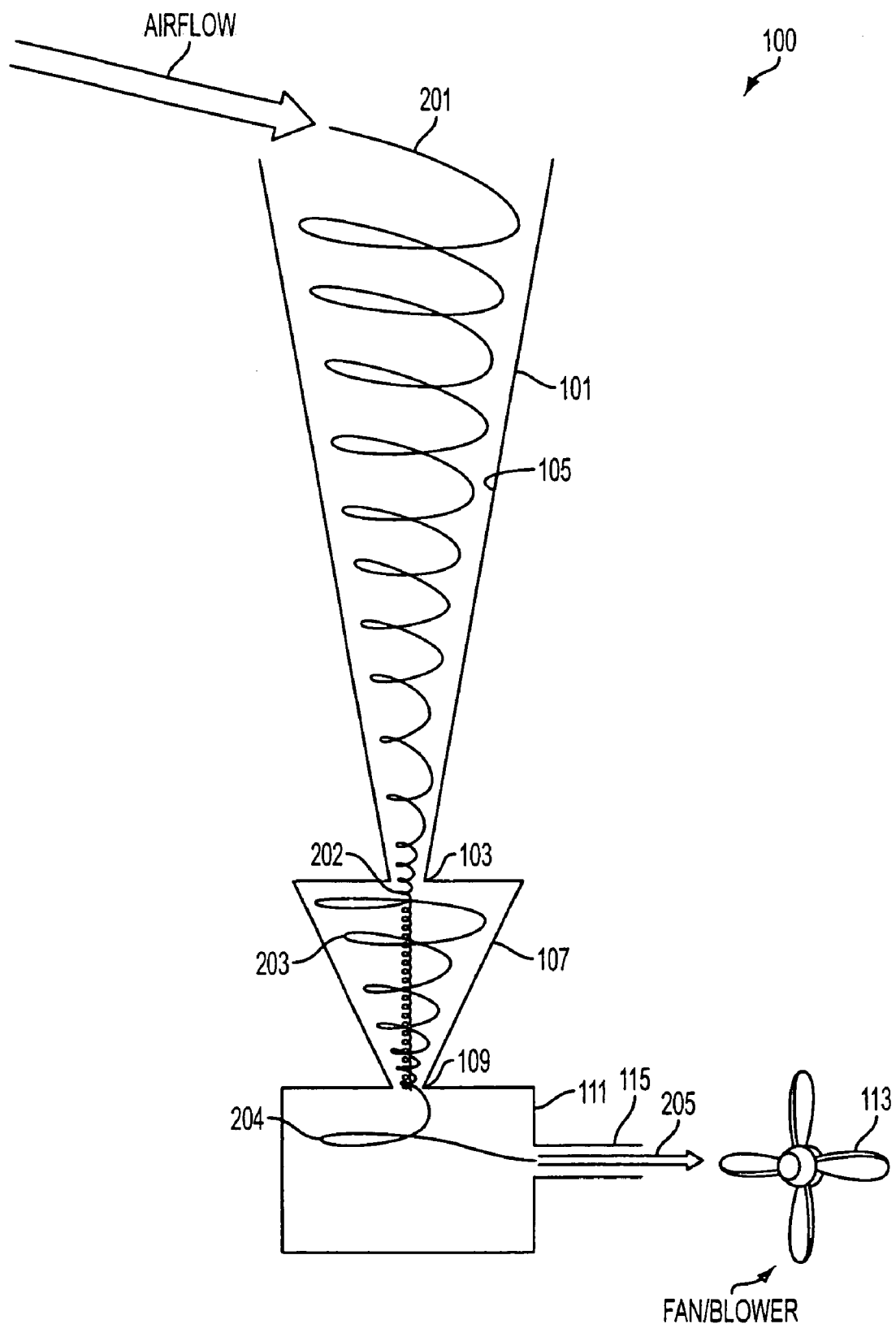
FIG. 2 provides a cutaway view of the embodiment of FIG. 1 showing the cyclonic air flow through the system.
Figure 3:
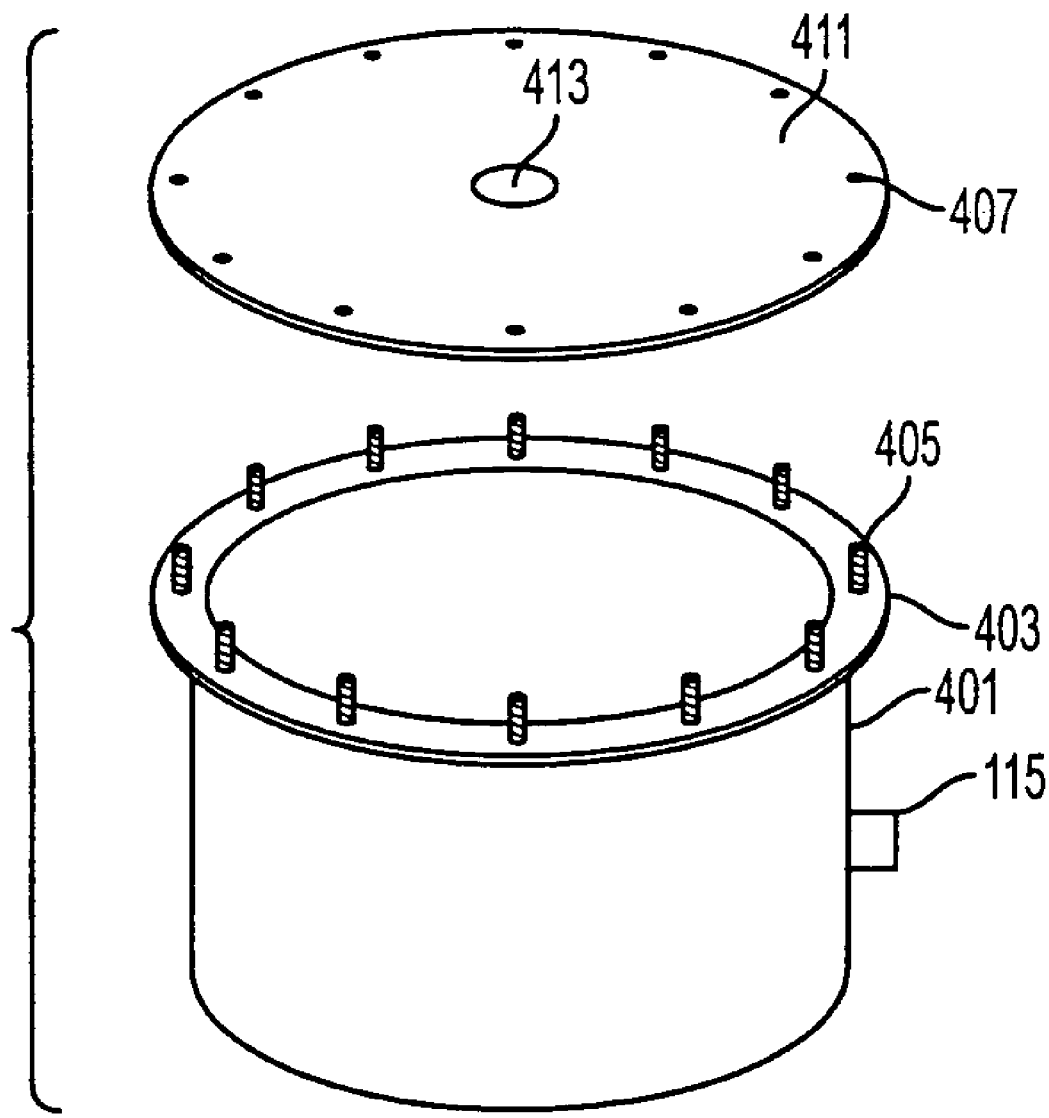
FIG. 3 provides an exploded perspective view of an embodiment of a secondary vortex break.

FIGS. 1 and 2 provide for different views of an embodiment of a cyclonic separator (100). The separator has three major components which in this embodiment are arranged vertically to each other. This arrangement provides a simple design for connection to related structures and other equipment, but the vertical orientation of the cyclone is not necessary to achieve proper performance. From the top to the bottom, a preferred embodiment includes a primary separator (101), a primary vortex break (107) and a secondary vortex break (111). While the preferred embodiment is arranged in this manner, the system can be rotated in space and still function. This arrangement, however, provides for benefits as gravity will help in the separation. Note that the sub-system comprised of the primary separator (101) and the primary vortex break (107) may, in an embodiment, be replaced by a primary separator (101) with no primary vortex break (107) being present. In an embodiment of the invention, the primary separator (101) may alternatively be comprised of a cyclonic separator of a type well known to those of ordinary skill in the art. Alternatively, in another embodiment, both the primary separator (101) and the vortex break (107) may be replaced by a cyclonic separator of a type well known in the art. Some of such cyclonic separators known in the art are shown and described in U.S. Pat. No. 6,596,046, the entire disclosure of which is herein incorporated by reference. In another embodiment, the entire cyclonic separator system (100) may be newly designed and built rather than incorporating designs already constructed. In a still further embodiment, a system of the prior art may be built or modified to include the roughened surface discussed later whether or not the primary vortex break (107) or secondary vortex break (111) is included.

The easiest way to understand the design of the system is to consider the air flow as it moves through the system. Generally an air flow (201) will be directed into the primary separator (101) from the top. The flow (201) will enter the primary separator (101) through an inlet pipe or other structure. The primary separator (101) will generally be comprised of a portion comprising an inverted cone. Generally, the primary separator (101) will be in the shape of a frustum of a cone, but need not be. The primary separator (101) may also include a generally cylindrical portion (not shown) attached to the top thereof. The primary separator's (101) shape combined with the air flow inlet geometry will induce the air flow (201) to spin creating a vortex or cyclone. Due to the rotation of the air stream, particles suspended in the air stream experience a centrifugal force causing them to move outward toward the interior wall (105) of the primary separator (101). Larger particles are forced out first and as the rotation becomes tighter, smaller and smaller particles are forced out. Particles reaching the interior wall (105) of the primary separator (101) are driven downward toward the first choke point (103) by the force of gravity and by the drag force from the downward component of the air flow. As the flow (201) approaches the choke point (103), the rotation of the air flow will accelerate leading to higher centrifugal forces causing smaller particles to be forced from the flow.

Also, as the cyclonic flow (201) approaches the first choke point (103) it begins to turn in on itself and travel up through the center of the cyclonic flow (201), eventually to exit out the top of the primary separator, generally through an exhaust tube (not shown). This change from a downward cyclonic flow to an upward cyclonic flow is caused by the relatively lower static pressure maintained in the center of the cyclonic flow (201) and in the exhaust tube, as well as by the shape of the primary separator (101). This flow reversal is generally completed inside the primary vortex break (107) into which the tip (202) of the cyclonic flow generally protrudes.

Particles that have been centrifuged out to the interior surface (105) of the primary separator (101) are moved down through the choke point by the force of gravity and by the drag force from the downward component of the air flow (201). Smaller particles are carried in the cyclonic flow (202) protruding into the primary vortex break (107). The larger of these smaller particles centrifuge out of the flow (202) inside the primary vortex break (107) (as the rotation is at its highest in flow (202)) while the smallest particles remain suspended in the flow and travel back up through the center of the cyclone to be exhausted. This action upon the particles traveling through the cyclone (101) and into the primary vortex break (107) acts as a high pass filter allowing a higher percentage of particles above a particular size to pass into the primary vortex break (107), being either centrifuged out of the air flow (202) or having been previously centrifuged out and pushed through the first choke point (103) by drag or gravity, while most of the particles below that size are exhausted out the top of the cyclone (101) from the upward cyclonic flow.

Particles passing through the first choke point (103) that are not drawn up to be exhausted, enter the primary vortex break (107) where centrifugal forces in the cyclonic air flow (202) cause these particles to be thrown out into the slower moving air (203) surrounding it. In this embodiment, the primary vortex break (107) is of a generally conical shape. The portion of the cyclonic flow (202) protruding down into the primary vortex break (107) maintains much of its slender tapered shape within the primary vortex break (107), much the same as a tornado's shape tapers as it approaches the ground. The primary vortex break (107) takes advantage of this phenomenon to separate additional particles from the flow (202).

Regarding the larger particles separated from the cyclonic air flow (201) in the primary separator (101), the large diameter at the top of the primary vortex break allows particles traveling downward along the cyclone wall (105) to separate themselves from the cyclonic flow (202) as they pass through the first choke point (103). Particles suspended in the flow (202) can also separate from that flow inside the primary vortex break (107) since the rate of rotation of the cyclonic flow (202) continues to produce a centrifugal force on the particles suspended therein. In both these cases, the separation is accomplished because the wall of the primary vortex break (107) is at some distance away from the cyclonic flow (202) and therefore cannot provide the centripetal force required to keep these particles in the flow (202).

Several outcomes may result for particles that separate from the flow (202) inside the primary vortex break (107). They may become suspended in slower moving air (203) within the primary vortex break (107), which is generally the case with the smaller particles separated in the primary vortex break from flow (202), or impact the interior wall of the primary vortex break (107) and travel downward toward the second choke point (109) in much the same way larger particles traveled in the primary separator (101). Larger particles may also impact the interior wall of the primary vortex break (107) and adhere to it. Preferably, the geometry of the primary vortex break (107) is designed to suspend most of the particles in the band of interest in the slower moving air (203). The resultant action within the primary vortex break (107), then, is a separation of the larger of the small particles left in the cyclonic air flow (202) after passing through the first choke point (103). The smallest particles, therefore, remain in the air flow (202) while larger particles are separated from the air flow (202). Both groups of particles will eventually enter the secondary vortex break (111) through the second choke point (109).

The secondary vortex break (111), as opposed to the primary vortex break (107), may be of any shape of sufficient dimensions to allow larger, uninteresting particles to settle out of the air flow (204) entering the secondary vortex break (111) under the influence of gravity before the air flow (204) exits through the output tube (115). Generally, this shape will be cylindrical but need not be and may be cubical, parallelepiped or any other volumetric shape. In a preferred embodiment, the secondary vortex break (111) will be generally cylindrical with a diameter in the range of 12 to 30 inches with a height between 10 and 20 inches. The specific shape or dimension will generally be selected to provide for uninteresting particles initially suspended in the air flow (204) and those passing into the secondary vortex break (111) not suspended in the air flow (204) to settle under the influence of gravity to the bottom of the secondary vortex break (111).

In operation, as the air flow (203) passes from the primary vortex break (107) through the second choke point (109), it is comprised of a portion of the cyclonic flow (202) and a portion of the slower moving air (203), which is generally also rotating, and contains both interesting and uninteresting particles. Along with this, larger particles, in contact with the interior wall of the primary vortex break (107), pass through the second choke point (109) under the influence of gravity and the drag force from the downward component of the air flow (203); some of these particles are retained in the air flow as they pass through the choke point (109) and the rest are drawn down to the bottom of the secondary vortex break (111) under the influence of gravity.

The air flow (204) enters the secondary vortex break as a thin stream of high speed air spiraling in the same direction as the air flow (201) in the primary separator (101). When this flow enters the larger diameter of the secondary vortex break (111), it is drawn to the perimeter of the secondary vortex break by the output flow (205) which is maintained by a fan (113), a blower, a pump, or a similar object. Therefore, the air flow (204) is made to travel for a duration of time in a more or less horizontal direction losing a significant amount of its cyclonic and rotational action. During this time, the effect of gravity is utilized to draw the heavier, uninteresting particles out of the flow and to the bottom of the secondary vortex break. Some of these particles, due to their inertia may be centrifuged from flow (204) and impact the inside wall of the secondary vortex break, but by this action, they too are effectively removed from the air stream (204). By adjusting the internal diameter (or bottom area depending on shape) of the secondary vortex break (111), the duration in which this mechanism is employed can be increased or decreased which will cause more or less large particles to be removed from the air flow (204) before the air flow is directed into the output tube (15) as flow (205). Namely, a larger diameter will generally result in smaller large particles separating while a smaller diameter will allow these smaller large particles to remain in the flow. The particles settling to the bottom of the secondary vortex break (111) are generally held there by gravity and are not reintrained in the air flow (204) because the air flow in the bottom of the secondary vortex break is relatively stagnant, having very little motion with which to disturb the layer of particles that accumulates there.

Thus, the air flow (204) contains a high concentration of particles in a particular band. The smaller particles (those below the band) have been mostly exhausted to atmosphere in the upward flow of the flow (201) in the primary separator (101) through the exhaust. The larger particles (those above the band) are separated from the air flow (204) and have been retained inside the secondary vortex break (111). Therefore, it can be said that the initial air flow (201) has undergone a band pass separation of particles and that the resulting air flow (205) contains a higher concentration of particles within a size band and a lower concentration of particles outside the band compared with the initial flow entering the system (201).

By locating the output tube (115) on the side of the secondary vortex break (111) instead of on the base and at a sufficient height and location about the perimeter of the secondary vortex break (111) and by selecting the dimensions of the secondary vortex break (111), the output tube (115) can capture the desired band of interesting particles carried in the air flow (204), or even a portion of the band carried by the air flow (204). The output flow (205) then transports these particles leaving the secondary vortex break (111) on a path to a detector or other processing equipment. In order to capture particles in air flow (204), an embodiment of the secondary vortex break (111) will preferably have the output tube (115) located anywhere from 1 to 12 inches vertically downward from the secondary choke point (109) depending on the band of particles desired and the size of the secondary vortex break (111). The specific characterization (e.g. particle size) of the band carried in air flow (205) can be adjusted, as would be understood by one skilled in the art, by altering the geometry of the primary separator (101), primary vortex break (107), and secondary vortex break (111) and the positioning of the outlet tube (115), as well as by altering flow rates and velocities of air flows (201) and (205).

Additionally, the secondary vortex break (111) and its output pipe (115) provide another unique function in that their geometry is capable of transforming a flow having relatively high cyclonic action (204) into one having relatively low cyclonic action (205). An air flow having relatively high cyclonic action cannot travel through a pipe or tube without losing a significant number of its suspended particles to the wall of the tube (115). This loss is caused by the high-speed rotation of the air flow within the tube (115) centrifuging the particles out to the interior surface of the tube (115) where they can adhere to the wall of the tube (115). If a tube (115) were connected directly to the output (109) of the primary vortex break (107) or even to the bottom (103) of the primary separator (101) body itself in an attempt to carry the high-pass particles to a detector, due to the continuing cyclonic motion of the air flow a significant number of particles in the band, as well as larger particles still suspended in the flow, would be centrifuged out to the wall of that tube (115) resulting in a significant reduction in the number of interesting particles reaching the detector.

The accumulated particles can also result in clogging of the tube (115) and decreased efficiency. By utilizing the geometry of the secondary vortex break (111) and its output tube (115), and connecting the secondary vortex break (111) to the output of the primary vortex break (109) or even to the output of the primary separator (101) itself, the cyclonic flow (201) traveling down the primary separator (101) is caused to change direction in the second vortex break (111) and exit more or less perpendicularly to the centerline of the cyclonic separator (100). The resultant air flow (205) comprises a relatively low cyclonic flow and therefore, can transport its suspended particles to a detector with significantly less loss to the wall of the tube (115) as compared with air flow that enters a tube (115) with a cyclonic or other rotational motion.

The output tube (115) of the secondary vortex break (111) may be arranged tangentially, radially, or anywhere in between relative to the side wall of the secondary vortex break (111), however, it is preferred that it be arranged generally radially thereto and located at the point where the particles of the desired size band begin to interact with the inside surface of the secondary vortex break (111). This radial arrangement generally provides for easier construction and improved suspended particle capture.

FIG. 3 shows an embodiment of a secondary vortex break (111) that may be used in a cyclonic separator as discussed above. This secondary vortex break (111) is cylindrical and may be attached to the primary vortex break (107) by any means known to one of ordinary skill in the art including, but not limited to, custom fittings, screw threads, welding, or unitary construction. This embodiment is comprised of a generally cylindrical main body (401) with an upper open surface and a closed base, the upper surface may have a lip (403) to facilitate connection to the lid (411), or the main body (401) may be connected to the lid (411) by some other method. In this embodiment, the upper surface or lip (403) is attached by a plurality of screws (405) which interact with a plurality of holes (407) on the top (411). Alternatively, the screws (405) may be replaced with pins or other types of connectors to hold the top (411) to the main body (401). The top (411) serves to cover the top of the main body (401) forming a generally enclosed cylinder. The main body (401) is, however, removable from the lid (411) to allow accumulated particles in the main body (large particles) to be disposed of. At or around the center of the top (411), there is a hole (413) which will serve to connect to the output of the primary vortex break (107). For this reason, the hole (413) will generally be sized and shaped to be of generally the same size as the choke point (109).

The band pass nature of the cyclonic separator (100) is particularly beneficial when the particulates of interest for analysis are known to be of a particular general size. Without the use of a secondary vortex break (111), larger, uninteresting particles are not removed and are fed into the output tube (115) along with those in the band of interest. This means that the uninteresting particles would either be carried through to the detector which leads to slower processing and decreased detector life or, along with some particles of interest, be deposited on the inside of the output pipe (115) which reduces the system's detection capability, decreases air flow to the detector, and increases the need for cleaning.

Even though one's best judgement and extreme care are utilized in the design and manufacture of the cyclonic separator (100) and its components, particles in the desired band can still be forced out of the air flow (201) and deposited on the inside surface of the primary separator (101) or on the inside surface of the primary vortex break (107). In these cases, particles of interest may be permanently prevented from reaching the detector in air flow (205). This can be especially problematic where very few particles of interest may be present in the air flow (201). While the system described above can concentrate particles into the band, some particles in the band may still be lost.

In an embodiment, this deposition can be reduced through the interior design of the primary separator (101), the primary vortex break (107), and even the secondary vortex break (111). In particular, if the interior surfaces of some or all of these items is made with a rough surface, the deposition of the particles of interest can be reduced, allowing more of these particles to pass into the next section of the cyclonic separator (100). This modification can also be used to reduce deposition in traditional cyclonic separators; however, it can be particularly beneficial in a band pass embodiment, such as that described above, as fewer particles of interest adhere to the wall.

In an embodiment in which the cyclonic separator (100) is used to improve the collection of particles in the 0.85 to 12 micron range (which can be useful for detection of respirable chemical or biological warfare agents), a surface roughness of 16 to 500 micro inches will generally be preferred. Such a roughness can lead to an improvement of from 30% to 400% over smooth surfaces depending on the particle size and various other factors. In testing, the rough surface has proven to be better than a smooth surface because the rough surface generally creates surface effect flows in the air flow (201) near the inner surface (105) of the cyclone (101). These surface effect flows increase a particle's momentum which helps prevent it from adhering to the surface (105) when it comes into contact with it. These flows, therefore, improve the chance of particles of interest being passed into the next component of the cyclonic separator (100). For a particle in the size band of interest, it is then more likely that the particle will travel through the system (100) and end up in air flow (204) and pass into the flow (205) and to the detector.

As would be understood by one of ordinary skill in the art, the particular size values of particles which pass through the high pass filter of the cyclone (101) and primary vortex break (107), and pass through the low pass filter of the secondary vortex break (111) are based on the relative diameters, sizes, and shapes selected for each of the components of the cyclonic separator (100), as well as the positioning of the output tube (115) relative to the base and diameter of the secondary vortex break (111). Further, previously discussed ranges are merely exemplary of certain ranges and are by no means intended to be exhaustive.

It should further be recognized that variations of this cyclonic separator system (100) can be combined together in parallel or series to provide multiple band pass ranges (having wider or narrower bands in each separator, as need be) to different detectors. For example, several cyclonic separators (100) could be designed to produce different band pass ranges in their output flows (205). These cyclones could be ganged together in parallel as a unit to sample particles from a common air stream but deliver the particles in different size ranges to different detectors.

Cyclones could also be connected in series by directing all or a portion of the output flow (205) into a cyclone (101) or into the primary vortex break (107) of a second cyclonic separator (100). Another method for connecting cyclones in series to provide multiple band pass ranges would direct the exhaust flow leaving the top of a cyclonic separator (101) into the intake flow (201) of a second cyclonic separator (100). In another example, the deposition in the secondary vortex break (111) above may be sent into a primary separator (101), or primary vortex break (107) of another cyclonic separator (100). These combined systems may then connect to additional cyclonic separators (100) as required, each providing a particular band pass separation from the initial air. Each of these cyclonic separators (100) may also have additional air flow (201) provided to them to provide improved operation and similar band pass separation to that above, but with a different band. The above described cyclonic separators (100) may also be used in conjunction with those of the prior art to provide both band pass and low or high pass separation together.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A cyclonic separator comprising:

a primary separator;

a primary vortex break attached to said primary separator at a first choke point; and a secondary vortex break, said secondary vortex break attached to said primary vortex break at a second choke point and having an output tube attached to a side thereof;

wherein said cyclonic separator separates particles in a particular band from other particles, said band having a minimum size greater than zero and a maximum size; and wherein an air flow including a concentration of said particles in said band flows into said output tube.

2. The separator of claim 1 further comprising a fan for pulling air and suspending particles into said output tube.

3. The separator of claim 1 wherein said secondary vortex break is not in the shape of an inverted cone.

4. The separator of claim 1 wherein said primary vortex break is generally in the shape of an inverted cone.

5. The separator of claim 1 wherein said primary separator is generally in the shape of an inverted cone.

6. The separator of claim 1 wherein the internal surface of said primary separator or said primary vortex break is rough.

7. The separator of claim 6 wherein said surface roughness is between about 16 and about 500 micro inches.

8. The separator of claim 1 wherein said minimum size is 0.85 micron.

9. The separator of claim 1 wherein said maximum size is 12 microns.

10. The separator of claim 1 wherein said separator is arranged vertically with said primary separator above said primary vortex break which is in turn above said secondary vortex break.

11. The separator of claim 10 wherein said separation is partially accomplished by the force of gravity.

12. The separator of claim 1 wherein said secondary vortex break is in the shape of a cylinder.

13. The separator of claim 12 wherein said output tube is arranged radially to said cylinder.

14. The separator of claim 12 wherein said output tube is arranged tangentially to said cylinder.

15. The separator of claim 1 wherein said output tube leads to a detector.

16. The separator of claim 1 wherein said concentration of said particles includes a chemical or biological warfare agent.

17. A method for cyclonic separation comprising:
forming a first air flow, said first air flow being cyclonic;
passing said air flow through a first choke point, said first air flow splitting into a second air flow which flows internal to said first air flow and a third air flow which interacts with slower moving air below said first choke point;
having said third air flow and slower moving air pass through a second choke point and into a secondary vortex break where said third air flow interacts with slower moving air below said second choke point;
drawing said air in said secondary vortex break outward; and
collecting at least a portion of said air which is drawn outward.

18. The method of claim 15 wherein said air which is drawn outward includes suspended particles.

19. The method of claim 16 wherein said suspended particles include chemical or biological warfare agents.

* * * * *